(12) United States Patent
Li et al.

(10) Patent No.: US 9,412,577 B2
(45) Date of Patent: Aug. 9, 2016

(54) VACUUM ULTRAVIOLET PHOTOIONIZATION AND CHEMICAL IONIZATION COMBINED ION SOURCE FOR MASS SPECTROMETRY

(75) Inventors: Haiyang Li, Dalian (CN); Lei Hua, Dalian (CN); Qinghao Wu, Dalian (CN); Huapeng Cui, Dalian (CN); Keyong Hou, Dalian (CN)

(73) Assignee: DALIAN INSTITUTE OF CHEMICAL PHYSICS, CHINESE ACADEMY OF SCIENCES, Dalian, Liaoning (CN)

( * ) Notice: Subject to any disclaimer, the term of this patent is extended or adjusted under 35 U.S.C. 154(b) by 6 days.

(21) Appl. No.: 13/884,081

(22) PCT Filed: Feb. 17, 2011

(86) PCT No.: PCT/CN2011/071043
§ 371 (c)(1),
(2), (4) Date: May 8, 2013

(87) PCT Pub. No.: WO2012/071806
PCT Pub. Date: Jun. 7, 2012

(65) Prior Publication Data
US 2013/0236362 A1  Sep. 12, 2013

(30) Foreign Application Priority Data
Nov. 30, 2010 (CN) .......................... 2010 1 0567193

(51) Int. Cl.
*H01J 49/16* (2006.01)
*G01N 27/64* (2006.01)
(Continued)

(52) U.S. Cl.
CPC .............. *H01J 49/161* (2013.01); *G01N 27/64* (2013.01); *G01N 30/72* (2013.01); *H01J 27/024* (2013.01);
(Continued)

(58) Field of Classification Search
CPC .................. G01N 2560/00; G01N 2021/6417; G01N 21/33; G01N 21/3504; G01N 27/622; H01J 49/10; H01J 49/40; H01J 49/00; H01J 49/004; H01J 49/061; H01J 49/168; H01J 49/424; H01J 49/4245

USPC ...................... 250/200, 389, 396 R; 356/326; 422/68.1, 82.08, 83, 500
See application file for complete search history.

(56) References Cited

U.S. PATENT DOCUMENTS 5,808,299 A     9/1998 Syage
6,509,562 B1 *  1/2003 Yang et al. ..................... 250/287
(Continued)

FOREIGN PATENT DOCUMENTS

CN    101063673 A    10/2007
CN    101329299 A    12/2008
(Continued)

OTHER PUBLICATIONS

Spanel and Smith. "Quantitative Selected Ion Flow Tube Mass Spectrometry: The Influence of Ionic Diffusion and Mass Discrimination", J Am Soc Mass Spectrom 2001, No. 12, p. 863-872.*
(Continued)

*Primary Examiner* — Dennis M White
*Assistant Examiner* — Bryan Kilpatrick
(74) *Attorney, Agent, or Firm* — Novick, Kim & Lee, PLLC; Allen Xue

(57) ABSTRACT

This invention relates to the field of mass spectrometry, and more specifically to a vacuum ultraviolet photoionization and chemical ionization combined ion source, which consists of a vacuum ultraviolet light source and an ion source chamber. An ion acceleration electrode, an ion repulsion electrode, an ion extraction electrode, and a differential interface electrode positioned inside the ion source chamber are arranged along the exit direction of the vacuum ultraviolet light beam in sequence and spaced, coaxial, and parallel from each other. The ion acceleration electrode, the ion repulsion electrode, the ion extraction electrode, and the differential interface electrode are all plate structures with central through holes. The vacuum ultraviolet light beam passes through the central through holes of the electrodes along the axial direction. By utilizing a single vacuum ultraviolet light source, the ion source is feasible to switch between two ionization modes, vacuum ultraviolet photoionization (VUV PI) and chemical ionization (CI), under suitable ion source pressure, thus greatly expanding the range of detectable samples.

15 Claims, 2 Drawing Sheets

(51) Int. Cl.
  H01J 49/26   (2006.01)
  G01N 30/72   (2006.01)
  H01J 27/24   (2006.01)
  H01J 49/00   (2006.01)
  H01J 49/10   (2006.01)
  H01J 27/02   (2006.01)
  H01J 49/14   (2006.01)

(52) U.S. Cl.
  CPC .............. *H01J 27/24* (2013.01); *H01J 49/00* (2013.01); *H01J 49/107* (2013.01); *H01J 49/145* (2013.01); *H01J 49/162* (2013.01); *H01J 49/26* (2013.01); *G01N 2560/00* (2013.01)

(56) References Cited

U.S. PATENT DOCUMENTS

| | | | |
|---|---|---|---|
| 6,727,499 | B2 | 4/2004 | Zimmermann et al. |
| 7,119,342 | B2 | 10/2006 | Syage et al. |
| 7,161,145 | B2 | 1/2007 | Oser et al. |
| 7,488,953 | B2 | 2/2009 | Fischer et al. |
| 7,642,510 | B2 | 1/2010 | McEwen |
| 7,910,883 | B2 | 3/2011 | Muehlberger et al. |
| 2005/0121607 | A1* | 6/2005 | Miller et al. .................. 250/287 |
| 2008/0048107 | A1 | 2/2008 | McEwen |

FOREIGN PATENT DOCUMENTS

| | | |
|---|---|---|
| CN | 101339161 A | 1/2009 |
| WO | 2005/001465 A1 | 1/2005 |

OTHER PUBLICATIONS

Chuang Chen, et al. "Bipolar Ionization Source for Ion Mobility Spectrometry Based on Vacuum Ultraviolet Radiation Induced Photoemission and Photoionization", Analytical Chemistry. Apr. 16, 2010, vol. 82 No. 10, pp. 4151-4157, ISSN 0003-2700, American Chemical Society, the United States.

Hua-Peng Hui, et al. "Development and Application of a Membrane Inlet-Single Photon Ionization-Mass Spectrometer for Online Analysis Volatile Organic Compounds in Water", Chinese Journal of Analytical Chemistry. May 31, 2010, vol. 8, No. 5, pp. 760-764, ISSN 0253-3820, American Chemical Society, the United States.

Lei Hua, et al., "Single Photon Ionization and Chemical Ionization Combined Ion Source Based on a Vacuum Ultraviolet Lamp for Orthogonal Acceleration Time-of-Flight Mass Spectrometry", Anal. Chem., 2011, 83, pp. 5309-5316, American Chemical Society, the United States.

Li Wang, et al., "Application of laser induced photoemission electron in time-of-flight mass spectrometry", Int. J. Mass Spectrom, 1998, 181, pp. 43-50, , Elsevier, Amsterdam.

Qinghao Wu, et al., "A combined single photon ionization and photoelectron ionization source for orthogonal acceleration time-of-flight mass spectrometer", Int. J. Mass Spectrom., 2010, 295, pp. 60-64, Elsevier, Amsterdam.

Luke Hanley, et al., "Light and Molecular Ions: The Emergence of Vacuum UV Single-Photon Ionization in MS", Anal. Chem., 2009, 81, pp. 4174-4182, American Chemical Society, the United States.

Gerardo Gamez, et al., "Photoelectron Emission as an Alternative Electron Impact Ionization Source for Ion Trap Mass Spectrometry", Anal. Chem., 2008, 80, pp. 6791-6795, American Chemical Society, the United States.

Fabian Muhlberger, et al. "Compact Ultrafast Orthogonal Acceleration Time-of-Flight Mass Spectrometer for On-Line Gas Analysis by Electron Impact Ionization and Soft Single Photon Ionization Using an Electron Beam Pumped Rare Gas Excimer Lamp as VUV-Light Source", Anal. Chem., 2007, 79, pp. 8118-8124, American Chemical Society, the United States.

Jack Syage, et al. "A Man-Portable, Photoionization Time-of-Flight Mass Spectrometer", Field Anal. Chem. Technol. 2000, 4, pp. 204-215, John Wiley & Sons, the United States.

\* cited by examiner

VACUUM ULTRAVIOLET PHOTOIONIZATION AND CHEMICAL IONIZATION COMBINED ION SOURCE FOR MASS SPECTROMETRY

FIELD OF THE INVENTION

This invention relates to the field of mass spectrometry, and more specifically to a vacuum ultraviolet photoionization and chemical ionization combined ion source. By utilizing a single vacuum ultraviolet light source, the ion source is feasible to switch between two ionization modes, vacuum ultraviolet photoionization (VUV PI) and chemical ionization (CI), under suitable ion source pressure, thus greatly expanding the range of detectable samples.

BACKGROUND OF THE INVENTION

Electron ionization (EI) source is the most widely used ion source in traditional organic mass spectrometry. EI uses 70-eV electrons to impact organic molecules, and ionizes them to obtain characteristic spectrum for each organic compound, thus realizing accurate qualitative analysis. However, the mass peaks are seriously overlapped while analyzing complex organic mixtures, because of the high degree of fragmentation of organic compounds with EI. Therefore, it's difficult for EI to achieve rapid and online analysis. Vacuum ultraviolet (VUV) light can be used as a soft ion source for organic compounds with ionization energies (IEs) lower than the photon energy, and is especially propitious for rapid qualitative and quantitative analysis, due to its high molecular ion yield and very low degree of fragmentation. Keyong Hou et. al. (Chinese invention patent No. 200610011793.2) and Peichao Zheng et. al. (Chinese invention patent No. 200810022557.X) have reported the online mass spectrometry with VUV PI ion source. The achieved mass spectra in the patents are simple, including only the molecular ion peaks of the investigated organic compounds, and these features are beneficial to rapid qualitative and quantitative analysis.

The energies of photons emitted from VUV light sources are limited by the optical window materials used in the light sources. The highest photon energy that can be transmitted by the currently available optical window material is 11.8 eV, by using the optical window material of LiF. Thus, organic molecules with IEs lower than 11.8 eV can be effectively ionized by VUV PI. However, some organic and inorganic compounds, such as methane ($CH_4$, IE=12.61 eV), acetonitrile ($CH_3CN$, IE=12.20 eV), sulfur dioxide ($SO_2$, IE=12.35 eV), and nitrous oxide ($N_2O$, IE=12.89 eV), cannot be ionized by the VUV photons emitted from the existing VUV light sources. Therefore, the applications of VUV PI mass spectrometry subject to certain restrictions.

SUMMARY OF THE PRESENT INVENTION

An object of the present invention is to provide a VUV PI and CI combined ion source for mass spectrometry, which combines CI mode into VUV PI source and ionizes molecules with IEs higher than the photon energy.

Accordingly, in order to accomplish the above objective, the present invention provides a VUV PI and CI combined ion source for mass spectrometry, wherein the combined ion source consists of a vacuum ultraviolet light source and an ion source chamber. The ion source chamber includes a gas vent on its side wall. A vacuum gauge is connected to a through hole on the side wall of the ion source chamber by means of a vacuum line.

An ion acceleration electrode, an ion repulsion electrode, an ion extraction electrode, and a differential interface electrode are positioned inside the ion source chamber. The vacuum ultraviolet light source emits vacuum ultraviolet light beam inside the ion source chamber. The ion acceleration electrode, the ion repulsion electrode, the ion extraction electrode, and the differential interface electrode are arranged along the exit direction of the vacuum ultraviolet light beam in sequence and spaced, coaxial, and parallel from each other.

A reagent gas sampling tube passes through the outer wall of the ion source chamber and inserts into the inner side of the ion source chamber. The gas outlet of the reagent gas sampling tube is located in the interspace between the ion acceleration electrode and the ion repulsion electrode and is orthogonal to the vacuum ultraviolet light beam, and the gas inlet of the reagent gas sampling tube is connected to a reagent gas source.

A sample gas sampling tube passes through the outer wall of the ion source chamber and inserts into the inner side of the ion source chamber. The gas outlet of the sample gas sampling tube is located in the interspace between the ion repulsion electrode and the ion extraction electrode and is orthogonal to the vacuum ultraviolet light beam, and the gas inlet of the sample gas sampling tube is connected to a sample gas source.

The ion acceleration electrode, the ion repulsion electrode, the ion extraction electrode, and the differential interface electrode are all plate structures with central through holes. The ion extraction electrode is one or more than one plate structure which is spaced, coaxial, and parallel from each other. The vacuum ultraviolet light beam passes through the central through holes of the electrodes along the axial direction of the electrodes.

A reactant ion region is located in the central zone between the ion acceleration electrode and the ion repulsion electrode, where reactant ions necessary for chemical ionization are generated. The length of said reactant ion region is in the range of 0.1 to 2 cm.

An sample ion region is located in the central zone between the ion repulsion electrode and the differential interface electrode, where vacuum ultraviolet photoionization and chemical ionization of sample molecules occur. The length of the sample ion region is in the range of 0.1 to 10 cm.

A series of voltages in the sequence from high to low are applied to the ion acceleration electrode, the ion repulsion electrode, the ion extraction electrode, and the differential interface electrode. The ion acceleration electric field formed along the axis direction of the reactant ion region is in the range of 5 to 500 V/cm. The ion extraction electric field formed along the axis direction of the sample ion region is in the range of 1 to 50 V/cm.

There is a restriction orifice in the central part of the ion repulsion electrode. The vacuum ultraviolet photons and ions in the reactant ion region are transferred into the sample ion region through the restriction orifice. The diameter of the restriction orifice is in the range of 0.5 to 5 mm.

The vacuum ultraviolet light source is a gas discharge lamp, or a laser-based light source, or a synchrotron light source.

There is a differential interface pinhole on the differential interface electrode and connected to a mass analyzer. The ions in the ion source chamber are transferred into the mass analyzer through the differential interface pinhole.

The mass analyzer is a time-of-flight mass analyzer, or a quadrupole mass analyzer, or an ion trap mass analyzer.

A gas vent is placed on the side wall of the ion source chamber and connected to an outlet valve through a vacuum line. A mechanical vacuum pump is connected to the other side of the outlet valve through another vacuum line.

The outlet valve is a flow adjustable vacuum valve. The outlet valve is a vacuum flapper valve, or a vacuum butterfly valve, or a vacuum needle valve.

The sample load and the pressure inside the ion source chamber can be adjusted by regulating the flow of the outlet valve, and the inner diameters and lengths of the reagent gas sampling tube and the sample gas sampling tube. The inner diameters of the reagent gas sampling tube and the sample gas sampling tube are in the range of 50 to 530 µm, and the lengths of the reagent gas sampling tube and the sample gas sampling tube are in the range of 5 to 500 cm. The sample load is in the range of 0.1 to 200 mL/min. The pressure inside the ion source chamber is in the range of $10^{-3}$ to 10 mbar.

DETAILED DESCRIPTION OF THE PREFERRED EMBODIMENT

Figure 1:
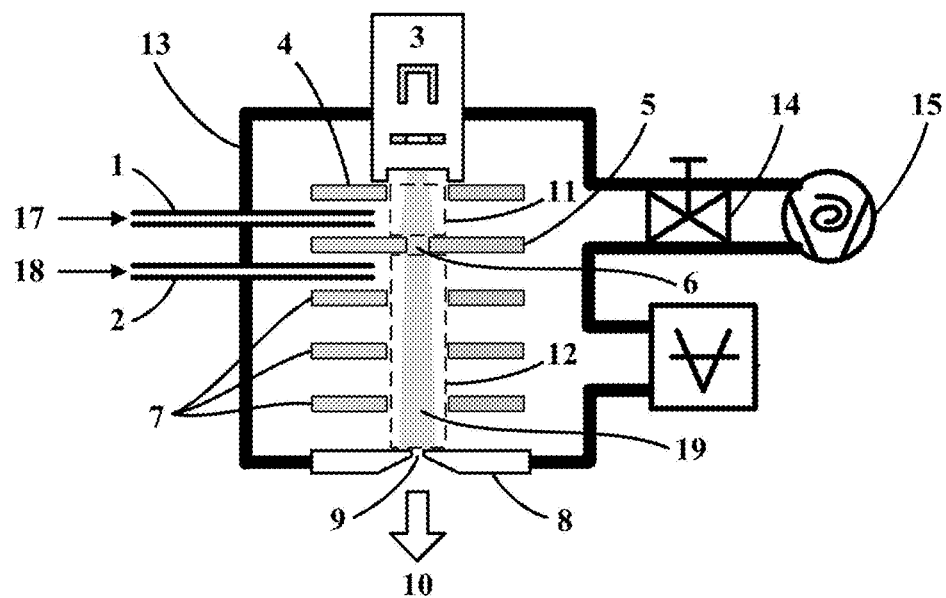
FIG. 1 is a schematic diagram of a VUV PI and CI combined ion source according to the invention.

Referring to FIG. 1, a schematic diagram of the presented invention is illustrated. A combined ion source provided in the present invention consists of a reagent gas sampling tube 1, a sample gas sampling tube 2, a vacuum ultraviolet light source 3, an ion acceleration electrode 4, an ion repulsion electrode 5, an ion extraction electrode 7, a differential interface electrode 8, and an ion source chamber 13.

The ion acceleration electrode 4, the ion repulsion electrode 5, the ion extraction electrode 7, and the differential interface electrode 8 are positioned inside the ion source chamber 13. The vacuum ultraviolet light source 3 emits vacuum ultraviolet light beam 19 inside the ion source chamber 3. The ion acceleration electrode 4, the ion repulsion electrode 5, the ion extraction electrode 7, and the differential interface electrode 8 are arranged along the exit direction of the vacuum ultraviolet light beam 19 in sequence and spaced, coaxial, and parallel from each other.

The reagent gas sampling tube 1 passes through the outer wall of the ion source chamber 13 and inserts into the inner side of the ion source chamber 13. The gas outlet of the reagent gas sampling tube 1 is located in the interspace between the ion acceleration electrode 4 and the ion repulsion electrode 5 and is orthogonal to the vacuum ultraviolet light beam 19, and the gas inlet of the reagent gas sampling tube 1 is connected to a reagent gas source 17.

The sample gas sampling tube 2 passes through the outer wall of the ion source chamber 13 and inserts into the inner side of the ion source chamber 13. The gas outlet of the sample gas sampling tube 2 is located in the interspace between the ion repulsion electrode 5 and the ion extraction electrode 7 and is orthogonal to the vacuum ultraviolet light beam 19, and the gas inlet of the sample gas sampling tube 2 is connected to a sample gas source 18.

The ion acceleration electrode 4, the ion repulsion electrode 5, the ion extraction electrode 7, and the differential interface electrode 8 are all plate structures with central through holes. The ion extraction electrode 7 is one or more than one plate structure which is spaced, coaxial, and parallel from each other. The vacuum ultraviolet light beam 19 passes through the central through holes of the electrodes along the axial direction of the electrodes.

A reactant ion region 11 is located in the central zone between the ion acceleration electrode 4 and the ion repulsion electrode 5, where reactant ions necessary for CI are generated. The length of said reactant ion region 11 is in the range of 0.1 to 2 cm. An sample ion region 12 is located in the central zone between the ion repulsion electrode 5 and the differential interface electrode 8, where VUV PI and CI of sample molecules occur. The length of the sample ion region 12 is in the range of 0.1 to 10 cm.

A series of voltages in the sequence from high to low are applied to the ion acceleration electrode 4, the ion repulsion electrode 5, the ion extraction electrode 7, and the differential interface electrode 8. The ion acceleration electric field formed along the axis direction of the reactant ion region 11 is in the range of 5 to 500 V/cm. The ion extraction electric field formed along the axis direction of the sample ion region 12 is in the range of 1 to 50 V/cm.

There is a differential interface pinhole 9 on the differential interface electrode 8 and connected to a mass analyzer 10. The ions in the ion source chamber 13 are transferred into the mass analyzer 10 through the differential interface pinhole 9.

Ambient sample gas and reagent gas are directly introduced into the ion source chamber 13 through two sampling tubes. The analytes are ionized by VUV PI or CI, and the product ions are directly transferred into the mass analyzer 10 through the differential interface pinhole 9 on the differential interface electrode 8. A mechanical vacuum pump 15 is connected to the rear end of an outlet valve 14 (flow adjustable vacuum valve) through a vacuum line. The excess gas molecules in the ion source chamber 13 are pumped away by the mechanical vacuum pump 15 through the outlet valve 14. The gas sample load is controlled by regulating the flow of the outlet valve 14 and the inner diameters and lengths of the reagent gas sampling tube 1 and the sample gas sampling tube 2. The pressure in the ion source chamber 13 is adjusted to induce enough collisions between ions and molecules in the ion source region, which meets the requirement of ion-molecule reactions in CI. The inner diameters of the reagent gas sampling tube 1 and the sample gas sampling tube 2 are in the range of 50 to 530 µm, and the lengths of the reagent gas sampling tube 1 and the sample gas sampling tube 2 are in the range of 5 to 200 cm. The gas sample load is in the range of 0.1 to 100 mL/min. The vacuum degree in the ion source chamber 13 is maintained at $10^{-3}$ to 10 mbar.

The combined ion source provided by the present invention is capable of fast switching between VUV PI mode and VUV PI-CI mode through simply regulating the sampling gas and the operation voltage of the ionization region. In VUV PI mode, only the sample gas is introduced to the sample gas sampling tube 2, and the molecules in the sample gas with IEs lower than the photon energy are ionized by VUV PI. The molecular ions of the analytes in the reactant ion region 11 and sample ion region 12 are extracted to the mass analyzer 10 through the differential interface pinhole 9, under the propulsion of weak ion acceleration electric field and ion extraction electric field.

In VUV PI-CI mode, the reagent gas and the sample gas are introduced to the reagent gas sampling tube 1 and the sample gas sampling tube 2, respectively. While the IE of the reagent gas is higher than the photon energy, the ion acceleration electric field in the reactant ion region 11 is enhanced, and the photoelectrons generated by irradiation of VUV light on the surfaces of metal electrodes are accelerated to high kinetic energies to impact with the reagent gas molecules and ionize them via EI. While the IE of the reagent gas is lower than the photon energy, the reagent gas molecules in the reactant ion region 11 are ionized by VUV PI under the propulsion of weak ion acceleration electric field. The reactant ions generated in the reactant ion region 11 enter the sample ion region 12 through a restriction orifice 6 in the central part of the ion repulsion electrode 5. The collisions between the reactant ions and the sample molecules in the sample ion region 12 lead to ion-molecule reactions under certain ion source pressure. The molecules in the sample gas with IEs higher than the photon energy are ionized by CI, while some of the molecules in the sample gas with IEs lower than the photon energy are ionized by VUV PI and the others by CI. The product ions obtained eventually are transferred into the mass analyzer 10 through the differential interface pinhole 9 and analyzed by the mass analyzer 10.

EXAMPLE 1

Figure 2:
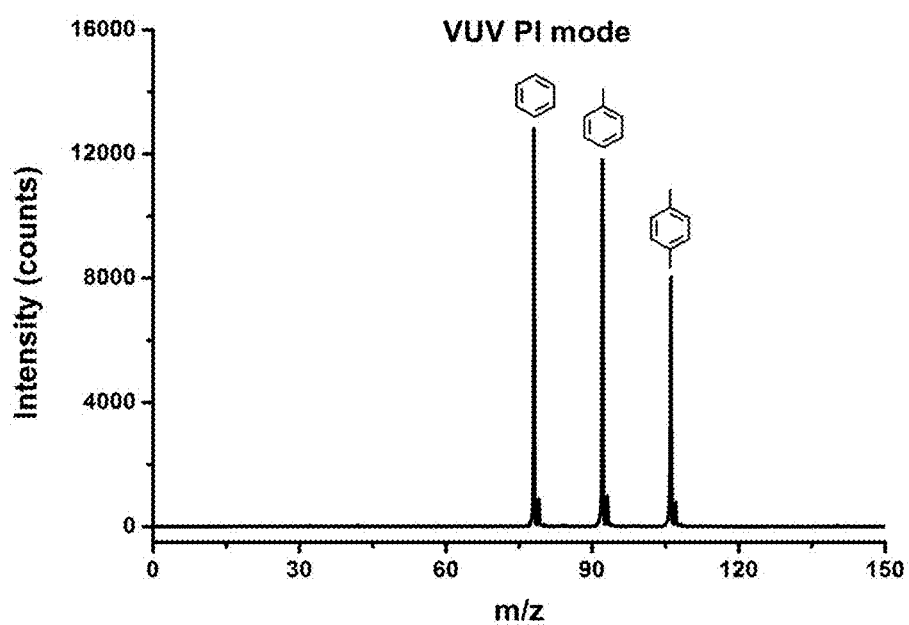
FIG. 2 shows the VUV PI mass spectrum of a benzene, toluene and p-xylene gas mixture with a respective concentration of 10 ppm in Example 1.

To investigate the performance of the combined ion source in VUV PI mode, a commercial krypton (Kr) lamp with the photon energy of 10.6 eV was used as the VUV light source. The combined ion source was coupled with a time-of-flight mass analyzer. Two 250 µm i.d., 100 cm long fused silica capillaries were used as the reagent gas sampling tube and the sample gas sampling tube, respectively. In VUV PI mode, the pressure in the ion source chamber was adjusted to 0.3 mbar, and the sample load was 30 mL/min. The strengths of the ion acceleration electric field and the ion extraction field were both set at 6 V/cm. FIG. 2 shows the VUV PI mass spectrum of a benzene (IE=9.24 eV), toluene (IE=8.83 eV) and p-xylene (IE=8.44 eV) gas mixture with a respective concentration of 10 ppm. As can be seen from the figure, the achieved mass spectrum is simple, containing mainly the molecular ion peaks of the organic constituents with IEs lower than the VUV photon energy by VUV PI, which is in favor of rapid and online qualitative and quantitative analysis of complex mixtures.

EXAMPLE 2

Figure 3:
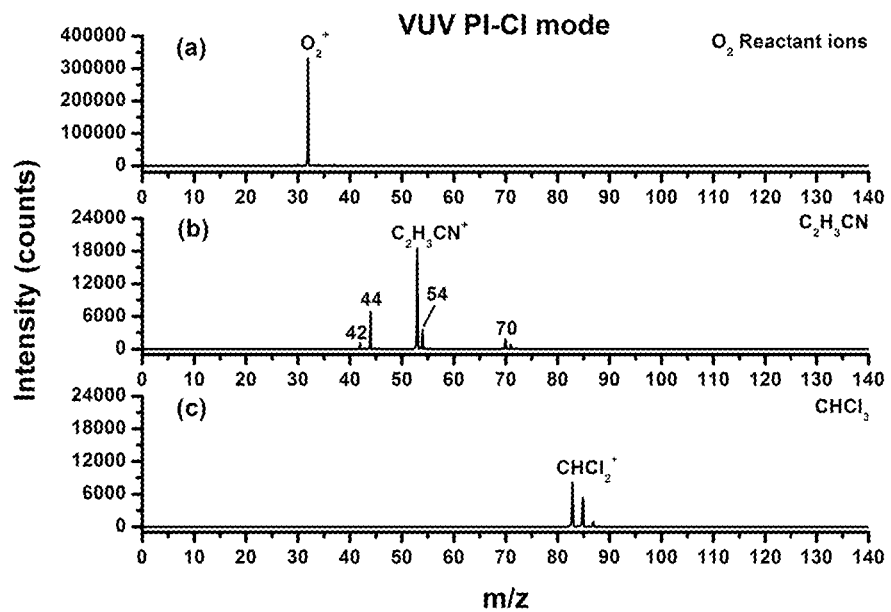
FIG. 3 shows the VUV PI-CI mass spectra of $O_2^+$ reactant ions (a), 10 ppm propenenitrile (b) and 10 ppm chloroform (c), while using $O_2$ as the reagent gas in Example 2.

To investigate the performance of the combined ion source in VUV PI-CI mode, oxygen ($O_2$, IE=12.07 eV) with IE higher than 10.6 eV and nitric oxide (NO, IE=9.26 eV) with IE lower than 10.6 eV were chosen as the reagent gas. Two 250 µm i.d., 100 cm long fused silica capillaries were used as the reagent gas sampling tube and the sample gas sampling tube, respectively. The pressure inside the ion source chamber was adjusted to 0.3 mbar, and the sample load was 30 mL/min. While $O_2$ was used as the reagent gas, high-purity $O_2$ (99.999%) was introduced into the reagent gas sampling tube, and a sample gas containing 10 ppm propenenitrile ($CH_3CN$, IE=12.20 eV) or 10 ppm chloroform ($CHCl_3$, IE=11.37 eV) was simultaneously introduced into the sample gas sampling tube. The strengths of the ion acceleration electric field and the ion extraction field were set at 100 V/cm and 6 V/cm, respectively. The acquired mass spectra are shown in FIG. 3. FIG. 3(a) shows mass spectrum of $O_2^+$ reactant ions obtained by introducing $O_2$ reagent gas alone, and FIG. 3(b) and FIG. 3(c) are the CI mass spectra of propenenitrile and chloroform with $O_2^+$ reactant ion peaks subtracted. It can be clearly seen that pure $O_2^+$ reactant ions with high intensity could be obtained from the combined ion source of the present invention, and molecules with IEs higher than the VUV photon energy were effectively ionized by CI by using $O_2^+$ as the reactant ions. The acquired mass spectra of the analytes contained only a few fragment ion peaks.

Figure 4:
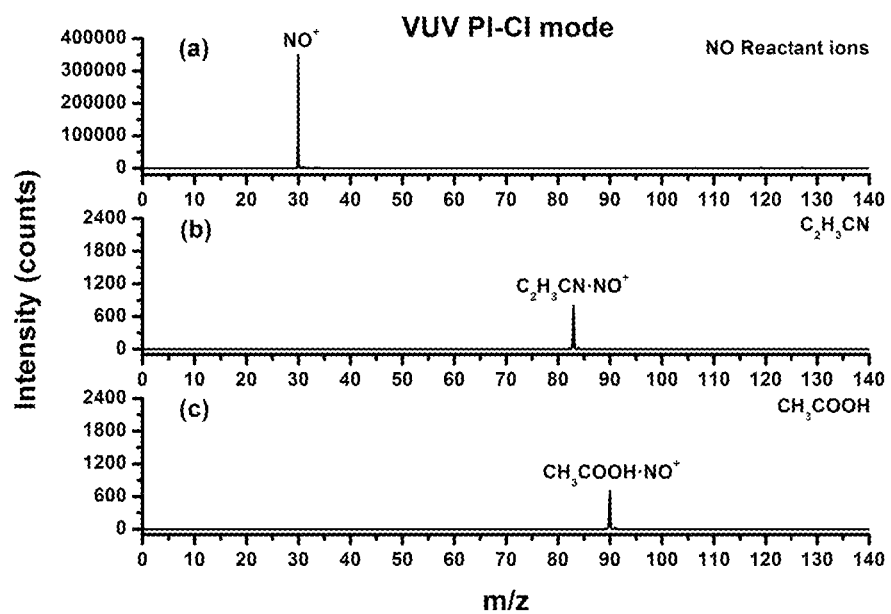
FIG. 4 shows the VUV PI-CI mass spectra of NO reactant ions (a), 10 ppm propenenitrile (b) and 10 ppm acetic acid (c), while using NO as the reagent gas in Example 2.

While NO was used as the reagent gas, 3% NO diluted in high-purity He was introduced into the reagent gas sampling tube, and a sample gas containing 10 ppm propenenitrile ($CH_3CN$, IE=12.20 eV) or 10 ppm acetic acid ($CH_3COOH$, IE=11.65 eV) was simultaneously introduced into the sample gas sampling tube. The pressure inside the ion source chamber was adjusted to 0.3 mbar, and the strengths of the ion acceleration electric field and the ion extraction field were both set at 6 V/cm. The acquired mass spectra are shown in FIG. 4. It can be clearly seen that pure $NO^+$ reactant ions with high intensity could be obtained from the combined ion source of the present invention either, and molecules with IEs higher than the VUV photon energy were effectively ionized by CI by using $NO^+$ as the reactant ions. The acquired mass spectra of the analytes M contained mainly peaks of quasi-molecular ion $[MNO]^+$.

What is claimed is:

1. An ion source, comprising:
   an ultraviolet light source for providing an ultraviolet light beam into an ion source chamber; and
   wherein the ion source chamber comprises:
   a first conduit for introducing a reagent gas into a reactant ion region;
   a second conduit for introducing a sample gas comprising an analyte into a sample ion region;
   a plurality of electrodes arranged along a path of the ultraviolet light beam, comprising an ion acceleration electrode, an ion repulsion electrode, an ion extraction electrode, and a differential interface electrode configured to be disposed at an interface with a mass analyzer;
   wherein the reactant ion region is located between the ion acceleration electrode and the ion repulsion electrode wherein reactant ions are generated by ionization of the reagent gas;
   wherein the sample ion region is located between the ion repulsion electrode and the differential interface electrode wherein analyte ions are generated by photoionization of the analyte, by chemical ionization between the reactant ions and the analyte, or both, and
   wherein the sample ion region is downstream from the reactant ion region along a direction of the ultraviolet light beam.

2. The ion source according to claim 1, wherein each of the ion acceleration electrode, the ion repulsion electrode, the ion extraction electrode, and the differential interface electrode is planar in shape and has a through hole, wherein the through holes in the electrodes are aligned to form a passage for the ultraviolet light beam.

3. The ion source according to claim 1, wherein a voltage of the ion acceleration electrode is greater than a voltage of the ion repulsion electrode, the voltage of the ion repulsion electrode is greater than a voltage of the ion extraction electrode, and the voltage of the ion extraction electrode is greater than a voltage of the differential interface electrode.

4. The ion source according to claim 1, wherein the through hole in the ion repulsion electrode is an orifice having a diameter of 0.5 to 5 mm.

5. The ion source according to claim 1, wherein said ultraviolet light source is a gas discharge lamp, a laser-based light source, or a synchrotron light source.

6. The ion source according to claim 1, wherein the ion source is connected to a mass analyzer and provides analyte ions to the mass analyzer, wherein said mass analyzer is a time-of-flight mass analyzer, a quadrupole mass analyzer, or an ion trap mass analyzer.

7. The ion source according to claim 1, further comprising a third conduit that operatively connects the ion source chamber to a vacuum pump.

8. The ion source according to claim 1, wherein the first conduit comprises a reagent gas sampling tube and the second conduit comprises a sample gas sampling tube, wherein the reagent gas sampling tube and the sample gas sampling tube have an inner diameter of 50 to 530 µm and a length of 5 to 500 cm.

9. The ion source according to claim 1, wherein the sample gas has a flow rate of 0.1 to 200 mL/min.

10. The ion source according to claim 1, wherein the ion source chamber has a pressure of $10^{-3}$ to 10 mbar.

11. The ion source according to claim 1, wherein the sample ion region has a length of 0.1 to 10 cm.

12. The ion source according to claim 1, wherein the sample ion region has an electric field in a range of 1 to 50 V/cm.

13. The ion source according to claim 1, where in the reactant ion region has a length of 0.1 to 2 cm.

14. The ion source according to claim 3, wherein the reactant ion region has an electric field in a range of 5 to 500 V/cm.

15. The ion source according to claim 1, comprising two or more ion extraction electrodes.

* * * * *